United States Patent [19]

Mueller et al.

[11] Patent Number: 5,342,853
[45] Date of Patent: Aug. 30, 1994

[54] METHOD OF USING NOR-VERAPAMIL AND NOR-GALLOPAMIL AS ANTI-ARTERIOSCLEROTICS

[75] Inventors: Claus D. Mueller, Viernheim; Liliane Unger, Ludwigshafen, both of Fed. Rep. of Germany

[73] Assignee: Knoll AG, Ludwigshafen, Fed. Rep. of Germany

[21] Appl. No.: 784,426

[22] Filed: Nov. 12, 1991

[30] Foreign Application Priority Data

Jun. 27, 1989 [DE] Fed. Rep. of Germany ....... 3921006

[51] Int. Cl.[5] .......................................... A61K 31/275
[52] U.S. Cl. ..................................... 514/523; 514/824
[58] Field of Search ................................ 514/523, 824

[56] References Cited

U.S. PATENT DOCUMENTS 3,261,859  7/1966  Dengel ................................ 558/390

FOREIGN PATENT DOCUMENTS 1154810  4/1964  Fed. Rep. of Germany .......... C07C 00/00

OTHER PUBLICATIONS

Cardiovascular Research, 1978, vol. 12, 247–254, G. Neugebauer.
Journal of Chromatography, vol. 413, 1987, 492–498.
Journal American College of Cardiology, 54, 884 (1984).

*Primary Examiner*—Marianne M. Cintins
*Assistant Examiner*—K. Weddington
*Attorney, Agent, or Firm*—Keil & Weinkauf

[57] ABSTRACT

The use of nor-verapamil and nor-gallopamil and the salts thereof with physiologically tolerated acids is disclosed for the preparation of drugs with antiarteriosclerotic properties.

3 Claims, No Drawings

METHOD OF USING NOR-VERAPAMIL AND NOR-GALLOPAMIL AS ANTI-ARTERIOSCLEROTICS

DESCRIPTION

The invention relates to the use of nor-verapamil (5-[N-(3,4-dimethoxyphenethyl)-amino]-2-(3,4-dimethoxyphenyl)-2-isopropyl-valeronitrile) and nor-gallopamil (5-[N-(3,4-dimethoxyphenethyl)-amino]-2-(3,4,5-trimethoxyphenethyl)-2-isopropyl-valeronitrile) for the preparation of drugs with antiarteriosclerotic properties.

Nor-verapamil is disclosed in the publication "Neugebauer, G., Cardiovasc. Rs. 1978, 12 (4) 247–254".

Nor-gallopamil is described by M. Nieder and H. Jaeger in Journal of Chromatography 1987, 414, 492–498.

Furthermore, German Patent 1,154,810 discloses verapamil (5-[N-(3,4-dimethoxyphenethyl)-N-methylamino]-2-(3,4-dimethoxyphenyl)-2-isopropyl-valeronitrile) and gallopamil (5-[N-(3,4-dimethoxyphenethyl)-N-methylamino]-2-(3,4,5-trimethoxyphenyl]-2-isopropyl-valeronitrile). The action of verapamil against arteriosclerosis has been investigated (JACC 1, 1453, 1983, Am. J. Cardiol. 54, 884, 1984).

It has now been found that nor-verapamil and nor-gallopamil have a very good action against arteriosclerosis.

The invention relates to the use of nor-verapamil and nor-gallopamil and the salts thereof with physiologically tolerated acids for the preparation of drugs with antiarteriosclerotic properties.

Nor-verapamil and nor-gallopamil can be used in free form. However, it is expedient to use them in the form of a salt with a physiologically tolerated acid (cf. German Patent 1,154,810).

Arteriosclerosis is a commonly occurring disorder, which is based on multifactorial causes, of the arterial vessel wall, as a consequence of which, owing to formation of atheromas, constriction of the vascular system and occlusions of vessels occur. The principal factors responsible for atheroma formation are:

- an increase in the permeability of the aortic endothelium for macromolecules (lipoproteins)
- migration of smooth muscle cells from association with the vessel intima, with subsequent proliferation and synthesis of ground substances (formation of arteriosclerotic plaques)
- migration of macrophages which absorb the excess infiltrating lipoproteins (foam cell formation).

It is possible with the compounds according to the invention to inhibit the formation of atheromas in the vessel wall and the progression of arteriosclerotic changes, or to promote the regression thereof.

To demonstrate the antiarteriosclerotic action, the substances are administered twice subcutaneously and once orally at intervals of 4 h in each case each day for 28 days to male rabbits. Local atheromas are induced by the method of E. Betz and W. Schlote (Basic Res. Cardiol. 1979, 74, 10–20) by electrical stimulation of the carotid artery while, at the same time, feeding a cholesterol-rich diet (2%). At the end of the test period, the atheromas formed under the anode of the stimulating electrodes are removed and their size is determined histologically. Used as a measure of the size of the atheromas is the maximum number of their cell layers determined microscopically from serial sections. The extent of the antiarteriosclerotic action is established by comparison with untreated control animals. Verapamil and gallopamil are used as comparative substances.

In this test, nor-verapamil and nor-gallopamil inhibit the development of atheromas to about the same extent as verapamil. Gallopamil has no antiatherogenic effect at the highest tolerated daily dose (Table 1). The Ca-antagonistic potency—determined from the binding to the Ca channel by displacement of the specific (S)-$^3$H-devapamil binding in membrane preparations from guinea pig skeletal muscles (Table 2)—is lower by factors of 8 and 10 than with verapamil and gallopamil respectively. Owing to their weak Ca-antagonistic action, the compounds according to the invention are distinctly superior to verapamil for the treatment of arteriosclerosis because they elicit no cardiovascular side effects at the same or a higher dosage.

Nor-verapamil and nor-gallopamil and the salts thereof can normally be administered orally or parenterally. The dosage depends on the age, condition and weight of the patient and on the mode of administration. As a rule, the daily dose of active substance is about 1 to 30, preferably 5 to 25 mg/kg of body weight on oral or rectal administration and 0.05–5, preferably 0.5 to 3 mg/kg of body weight on parenteral administration.

The substances have a center of asymmetry and are suitable for resolution into enantiomers.

The resulting compounds according to the invention are, where appropriate, converted into the acid addition salt of a physiologically tolerated acid. A list of conventional physiologically tolerated acids can be found in Fortschritte der Arzneimittelforschung 1966, Deutschland, Schweiz, Birkhäuser Verlag, Vol. 10, pp. 224–285 and J. Pharm. Sci. Vol. 66 (1977), pp. 1–5. Hydrochloric acid is preferred.

The acid addition salts are, as a rule, obtained in a manner known per se by mixing the free base or solutions thereof with the relevant acid or solutions thereof in an organic solvent, for example a lower alcohol such as methanol, ethanol or propanol, or a lower ketone such as acetone, methyl ethyl ketone or methyl isobutyl ketone, or an ether such as diethyl ether, tetrahydrofuran or dioxane. Mixtures of said solvents can be used to improve crystallization. In addition, pharmaceutically acceptable aqueous solutions of acid addition compounds of the amino compounds of the formula I can be prepared by dissolving the free bases in an aqueous acid solution.

Nor-verpamil (sic) and nor-gallopamil and the salts thereof can be used solid or liquid in the conventional pharmaceutical administration forms, e.g. in the form of tablets, film-coated tablets, capsules, powders, granules, sugar-coated tablets, suppositories, solutions or metered aerosols. The latter are produced in the conventional manner. The active substances can in this connection be processed with the conventional pharmaceutical auxiliaries such as tablet binders, fillers, preservatives, tablet disintegrants, flow regulators, plasticizers, wetting agents, dispersants, emulsifiers, solvents, retardants and/or antioxidants (cf. H. Sucker et al.: Pharmazeutische Technologie, Thieme-Verlag, Stuttgart 1978). The formulations obtained in this way normally contain the active substance in an amount of 3 from 0.1 to 99% by weight.

EXAMPLES 1 AND 2

Tablets of the following composition are pressed in a tablet press in a conventional manner:
- 40 mg of nor-verapamil hydrochloride (Ex. 1) or nor-gallopamil hydrochloride (Ex. 2)
- 120 mg of corn starch
- 13.5 mg of gelatin
- 45 mg of lactose
- 2.25 mg of Aerosil ® (chemically pure silica in sub-microscopically fine dispersion
- 6.75 mg of potato starch (as 6% paste)

EXAMPLES 3 AND 4

Sugar-coated tablets of the following composition are produced in a conventional manner:
- 20 mg of nor-verapamil hydrochloride (Ex. 3) or nor-gallopamil hydrochloride (Ex. 4)
- 60 mg of core composition
- 60 mg of sugar-coating composition.

The core composition consists of 9 parts of corn starch, parts of lactose and 1 part of 60:40 vinylpyrrolidone/vinyl acetate copolymer (cf. Pharm. Ind. 1962, 586). The sugar-coating composition consists of 5 parts of sucrose, 2 parts of corn starch, 2 parts of calcium carbonate and 1 part of talc. The sugar-coated tablets produced in this way are subsequently provided with an enteric coating.

EXAMPLES 5 AND 6

10 g of nor-verapamil hydrochloride (Ex. 5) or nor-gallopamil hydrochloride (Ex. 6) are dissolved in 5,000 ml of water with the addition of NaCl and adjusted to pH 6.0 with 0.1 normal NaOH to produce a solution which is isotonic with blood. 5 ml portions of this solution are dispensed into ampoules and sterilized.

TABLE 1

| | Antiatherogenic action on rabbits | | | | |
|---|---|---|---|---|---|
| | Daily dose | | Number of animals | Maximum number of cell layers in the atheromas | |
| | mg/kg | | | | |
| Substance | s.c. | oral | N | n | % change |
| Verapamil | — | — | 5 | 7.8 ± 1.0 | −51 |
| | 2 × 1.0 | 21.5 | 5 | 3.8 ± 0.37* | |
| Nor-verapamil | — | — | 8 | 14 ± 2.4 | −40 |
| | 2 × 1.0 | 21.5 | 8 | 8.1 ± 1.3 1) | |
| Gallopamil | — | — | 9 | 14 ± 1.2 | +7.1 |
| | 2 × 0.215** | 4.64** | 9 | 15 ± 0.99 | |
| Nor-gallopamil | — | — | 6 | 22 ± 3.2 | −44 |
| | 2 × 1.0 | 21.5 | 7 | 12 ± 1.3* | |

*P < 0.05
1) P = 0.682
**highest tolerated daily dose

TABLE 2

| | Binding to the calcium channel |
|---|---|
| Substance | $K_i$ (nM) (S)-$^3$H-devapamil displacement |
| Verapamil | 41 |
| Nor-verapamil | 320 |
| Gallopamil | 24 |
| Nor-gallopamil | 247 |

Membrane homogenate is incubated with increasing concentrations ($10^{-10}$–$10^{-6}$M) of test substance and a fixed concentration of 1 nM radioligand at room temperature for 60 min. The bound and the free radioligand are separated by filtration through glass fiber filters, and the amount of radioligand retained on the filter is determined by liquid scintillation measurement. 2 experiments in triplicate are carried out.

The competition constant ($K_i$ values in nM) is calculated by non-linear regression analysis on an IBM computer based on the ligand program of Munson and Rodboard (Analytical Biochemistry 107, 220, 1980).

We claim:

1. A method for treating patients suffering from arteriosclerosis, which comprises administering orally an antiarteriosclerotic dose of nor-verapamil or nor-gallopamil to said patients.

2. A method according to claim 1 for treating patients suffering from arteriosclerosis, which comprises administering orally an antiarteriosclerotic dose of nor-verapamil to these patients.

3. A method according to claim 1 for treating patients suffering from arteriosclerosis, which comprises administering orally an antiarteriosclerotic dose of nor-gallopamil to these patients.

* * * * *